(12) United States Patent
Arimura et al.

(10) Patent No.: US 8,481,673 B2
(45) Date of Patent: Jul. 9, 2013

(54) BIO-DEGRADABLE/ABSORBABLE POLYMER HAVING REDUCED METAL CATALYST CONTENT, AND PROCESS FOR PRODUCTION THEREOF

(71) Applicant: Gunze Limited, Ayabe (JP)

(72) Inventors: Hidetoshi Arimura, Ayabe (JP); Yoshitake Takahashi, Ayabe (JP); Koji Yamauchi, Ayabe (JP)

(73) Assignee: Gunze Limited, Ayabe-shi, Kyoto (JP)

( * ) Notice: Subject to any disclaimer, the term of this patent is extended or adjusted under 35 U.S.C. 154(b) by 0 days.

(21) Appl. No.: 13/624,207

(22) Filed: Sep. 21, 2012

(65) Prior Publication Data

US 2013/0066042 A1 Mar. 14, 2013

Related U.S. Application Data

(62) Division of application No. 12/305,104, filed as application No. PCT/JP2007/062212 on Jun. 18, 2007, now abandoned.

(30) Foreign Application Priority Data

Jun. 28, 2006 (JP) ................. 2006-178805
Jun. 28, 2006 (JP) ................. 2006-178808

(51) Int. Cl.
*C08G 63/08* (2006.01)
(52) U.S. Cl.
USPC ............ 528/354; 528/357; 528/361; 528/499
(58) Field of Classification Search
USPC .......................................... 528/354, 355, 499
See application file for complete search history.

(56) References Cited

U.S. PATENT DOCUMENTS

| | | |
|---|---|---|
| 4,045,418 A | 8/1977 | Sinclair |
| 4,643,734 A | 2/1987 | Lin |
| 4,810,775 A | 3/1989 | Bendix et al. |
| 4,960,866 A | 10/1990 | Bendix et al. |
| 5,359,027 A | 10/1994 | Perego et al. |
| 5,386,004 A | 1/1995 | Obuchi et al. |

FOREIGN PATENT DOCUMENTS

| | | |
|---|---|---|
| EP | 0 591 978 A2 | 4/1994 |
| EP | 1 334 990 A1 | 8/2003 |
| JP | 60-501217 A | 8/1985 |
| JP | 63-145327 A | 6/1988 |
| JP | 63-254128 A | 10/1988 |
| JP | 6-501045 A | 2/1994 |
| JP | 6-116381 A | 4/1994 |
| JP | 6-256492 A | 9/1994 |
| JP | 7-102053 A | 4/1995 |
| JP | 9-263629 A | 10/1997 |
| JP | 2000-191753 A | 7/2000 |
| JP | 2006-182999 A | 7/2006 |
| JP | 2007-70413 A | 3/2007 |
| WO | 92/04393 A1 | 3/1992 |

OTHER PUBLICATIONS

Chinese Office Action dated Dec. 1, 2010, issued in corresponding Chinese Patent Application No. 200780022257.5, with English Translation.
European Search Report dated Nov. 29, 2010, issued in corresponding European Patent Application No. 07745462.7.
J. Knapek et al., "Determination of Tin in Canned Foods by Atomic Adsorption Spectrometry", Czech J. Food Sci, Oct. 2009, S407-S409, vol. 27.
International Search Report of PCT/JP2007/062212, Mailing Date of Aug. 14, 2007.

*Primary Examiner* — Gregory Listvoyb
(74) *Attorney, Agent, or Firm* — Westerman, Hattori, Daniels & Adrian, LLP

(57) ABSTRACT

The present invention provides a method for reducing the content of a metal catalyst in a biodegradable and absorbable polymer that can be applied on an industrial scale and a method for producing a biodegradable and bioabsorbable polymer having a metal catalyst content of less than 1 ppm in terms of a metal. The method includes the steps of (1) copolymerizing lactide and ε-caprolactone at a molar ratio ranging from 40/60 to 60/40 or 65/35 to 85/15 in the presence of the metal catalyst to produce a copolymer; and (2) washing the copolymer with a mixed solvent comprising acetic acid and isopropanol at a volume ratio ranging from 25/75 to 45/55 or 45/55 to 55/45 at less than 40° C., and drying the copolymer.

16 Claims, 1 Drawing Sheet

BIO-DEGRADABLE/ABSORBABLE POLYMER HAVING REDUCED METAL CATALYST CONTENT, AND PROCESS FOR PRODUCTION THEREOF

CROSS-REFERENCE TO RELATED APPLICATIONS

This is a divisional application of U.S. patent application Ser. No. 12/305,104, filed on Dec. 16, 2008, which is a 371 of International Application No. PCT/JP2007/062212, filed on Jun. 18, 2007, which claims the benefit of priority from the prior Japanese Patent Application Nos. 2006-178805, filed on Jun. 28, 2006 and 2006-178808 filed on Jun. 28, 2006, the entire contents of which are incorporated herein by references.

TECHNICAL FIELD

The present invention relates to a biodegradable and bioabsorbable polymer having a low metal catalyst content (residual content), and a process for producing the same. Specifically, the invention relates to a technique for reducing the content of the metal catalyst in the biodegradable and bioabsorbable polymer obtained after synthesis using the metal catalyst.

BACKGROUND ART

Known examples of biodegradable and bioabsorbable polymers include polylactic acid, polyglycolic acid, polycaprolactone, trimethylene carbonate, polydioxane, copolymers thereof, and the like. They are degradable and absorbable in vivo, and are thus used in medical implant applications such as sutures, bone-joining materials, etc.

Since a heavy metal-based catalyst such as tin octylate is widely used for the synthesis of such a polymer compound, the metal catalyst remains in the synthesized polymer compound. When the polymer compound is used as a material for a medical implant application, the metal catalyst is exposed to the body with the degradation of the polymer. The metal catalyst, which varies according to species, may have harmful effects on the human body such as immunotoxicity, genetic toxicity, neurotoxicity, etc. when present at a certain concentration or more. Therefore, when the polymer is used in a medical implant application, the metal catalyst residual content must be reduced as much as possible.

On the other hand, polymers for implant applications require features of a certain level or more of molecular weight, strength, etc. In order to obtain such polymers, a metal catalyst of a certain amount or more must be added during the polymerization process; it is thus required to remove the metal catalyst remaining in the polymer after the polymerization reaction. However, removal of the metal catalyst is not easy, and is often accompanied by industrial difficulties.

For example, in a method described in Patent Document 1, a polymer compound is first dissolved in an organic solvent, and a metal catalyst is then removed by reprecipitation. This method, however, requires a large amount of solvent, and causes a drastic drop in molecular weight due to the polymer dissolution. Therefore, this is not appropriate for producing materials (e.g., medical devices) that require strength of a certain level or more. Furthermore, since the polymer tends to contain many air bubbles when reprecipitated, the molded product of the polymer is also likely to contain bubbles. Thus, it is not suitable for industrial manufacture.

Patent Document 2 discloses a method for producing copolymers of lactide and ε-caprolactone; however, it does not disclose the final metal catalyst content. The publication discloses that the catalyst is used in an amount of $10^{-7}$ to $10^{-3}$ mol/mol relative to the monomers; however, the Examples merely disclose that a catalyst is added in an amount of $10^{-5}$ mol (metal content: 22 ppm) per mol of monomer. The further reduction of the metal catalyst content is not specifically disclosed.

Patent Document 3 discloses a method for obtaining a biodegradable and bioabsorbable polymer having a high molecular weight by adding 1 to 20 ppm of a metal catalyst and 0.01 to 0.5 wt % of higher alcohol to lactide and caprolactone, and by conducting polymerization under reduced pressure for 10 to 40 days. However, since the end of the polymer obtained by this method is modified with a higher alcohol, it is considered that the polymer has different properties (e.g., absorbability, safety) than previously used bioabsorbable polymers, and thus various examinations are required. Furthermore, since the metal catalyst content used is too small, a long polymerization period is required. It is therefore not industrially preferable.

Patent Document 1:
Japanese Unexamined Patent Publication No. S60-501217, see Example I, etc.
Patent Document 2:
Japanese Unexamined Patent Publication No. H6-501045
Patent Document 3:
Japanese Unexamined Patent Publication No. 2000-191753

DISCLOSURE OF THE INVENTION

The object of the present invention is to provide a safe biodegradable and bioabsorbable polymer having an extremely low metal catalyst content, while retaining the properties desired for a medical implant or the like; and a process for producing the same. The present invention further aims to provide a method for reducing the content of a metal catalyst in a biodegradable and absorbable polymer that can be applied on an industrial scale.

Method for Solving the Problems

The present inventors conducted extensive research to achieve the above objects. As a result, they found that a biodegradable and bioabsorbable polymer that is obtained by copolymerizing lactide (lactic acid cyclic dimer) and ε-caprolactone at a specified molar ratio in the presence of a metal catalyst is capable of having a metal catalyst content of less than 1 ppm in terms of a metal by washing the polymer with the mixed solvent containing acetic acid and isopropanol at a specified volume ratio.

Specifically, the present inventors found that the metal catalyst can be effectively removed, without causing a drastic drop in molecular weight, by copolymerizing lactide (lactic acid cyclic dimer) and ε-caprolactone at a molar ratio ranging from 40/60 to 60/40 using a metal catalyst to produce a copolymer, and washing the copolymer with a mixed solvent comprising acetic acid and isopropanol at a volume ratio ranging from 25/75 to 45/55, and drying the copolymer. Hereinafter, this invention is sometimes referred to as "First Embodiment".

The present inventors further found that the metal catalyst can be effectively removed, without causing a drastic drop in molecular weight, by copolymerizing lactide (lactic acid cyclic dimer) and ε-caprolactone at a molar ratio ranging from 65/35 to 85/15 using a metal catalyst to produce a copolymer, and washing the copolymer with a mixed solvent comprising acetic acid and isopropanol at a volume ratio ranging from 45/55 to 55/45, and drying the copolymer. Hereinafter, this invention is sometimes referred to as "Second Embodiment".

The invention is explained below in full detail.

First Embodiment

1. Biodegradable and Bioabsorbable Polymer

The biodegradable and bioabsorbable polymer of the present invention is a lactide/ε-caprolactone copolymer, which comprises lactide and ε-caprolactone at a molar ratio ranging from 40/60 to 60/40, and preferably 45/55 to 55/45.

The biodegradable and bioabsorbable polymer of the invention has a weight average molecular weight (Mw) of about 50,000 to about 800,000, and particularly about 100,000 to about 500,000. Within the range described above, the polymer is suitably used as a medical implant in view of properties such as strength, degradability, and processability.

A metal included in the biodegradable and bioabsorbable polymer is derived from a metal catalyst used in a polymerization reaction for producing the biodegradable and bioabsorbable polymer mentioned below. Examples of such metals include sodium, potassium, aluminium, titanium, zinc, tin, etc. For example, when tin octylate is used in the polymerization reaction, tin will be the main metal contained in the polymer.

The biodegradable and bioabsorbable polymer of the present invention has an extremely low metal catalyst content of less than 1 ppm in terms of a metal. The content of the metal catalyst (in terms of a metal) in the polymer is preferably 0.1 to 0.95 ppm, more preferably 0.1 to 0.7 ppm, and further preferably 0.1 to 0.5 ppm. Thus, even when the biodegradable and bioabsorbable polymer of the invention is used as a medical implant, there is little possibility of causing immunotoxicity, genetic toxicity, neurotoxicity, etc. in the human body.

The metal catalyst content (in terms of a metal) is measured as follows. A sulfuric acid/nitric acid mixture (1:1, volume ratio) is added to the polymer, and then heated to degrade an organic component. Metal in the resulting mixture is quantified using a plasma emission spectrometry machine with reference to a metal standard solution. Test Example I-1(1) illustrates a measurement example in which tin octylate is used as a catalyst.

2. Production of Biodegradable and Bioabsorbable Polymer

The biodegradable and bioabsorbable polymer of the present invention having a low metal catalyst content is produced by polymerizing lactide and ε-caprolactone in the presence of a metal catalyst to produce a copolymer, washing the copolymer with a mixed solvent comprising acetic acid and isopropanol at a volume ratio ranging from 25/75 to 45/55, and drying the copolymer. According to the production method, the metal catalyst content (in terms of a metal) in the biodegradable and bioabsorbable polymer can be reduced to less than 1 ppm.

The production method is explained in detail below.

(1) Production of Copolymer

The copolymer is produced by copolymerizing lactide and ε-caprolactone in the presence of a metal catalyst.

A lactic acid forming the lactide may be any one of the following: L-form, D-form, or DL-form, but is preferably L-form.

Examples of metal catalysts include those containing sodium, potassium, aluminium, titanium, zinc, tin, or like groups. Specific examples include sodium ethoxide, potassium-t-butoxide, triethylaluminum, tetrabutyl titanate, tin octylate (II), tin 2-ethylhexanoate, triphenyltin acetate, tin oxide, dibutyltin oxide, tin oxalate, tin chloride, dibutyltin dilaurate, etc. Of these, tin octylate (II) is preferable in view of reactivity and safety in the polymerization reaction.

The used amount of the metal catalyst is about 100 to about 1,000 ppm (about 29 to about 290 ppm in terms of a metal), and preferably about 200 to about 700 ppm (48 to 203 ppm in terms of a metal) relative to the mixture weight content of lactide and ε-caprolactone.

By using the metal catalyst in the range described above, a copolymer that has a molecular weight, strength, or like properties suitable for implant applications can be produced in a shorter period of time. When the amount of metal catalyst to be added is too small, a large number of monomers remain unreacted, or the reaction requires too much time, resulting in a polymer that is unsuitable for industrial manufacture. Further, a polymer having a large polymerization degree (a high molecular weight) cannot be obtained, and it is thus not preferable.

The copolymer can be produced by subjecting lactide and ε-caprolactone to a publicly known polymerization reaction such as bulk polymerization, in the presence of a metal catalyst. Specifically, the lactide and ε-caprolactone are introduced in a reaction vessel, and then the metal catalyst is added thereto such that the metal catalyst is contained in an amount of about 200 to about 700 ppm (48 to 203 ppm in terms of a metal). Bulk polymerization is then carried out under a nitrogen atmosphere, or under reduced pressure according to a known method for 2 to 20 days at 110 to 180° C.

The weight average molecular weight (Mw) of the resulting lactic acid-ε-caprolactone copolymer is about 50,000 to about 800,000, and preferably about 100,000 to about 500,000.

At this stage, the content of the metal catalyst (in terms of a metal) in the copolymer is equivalent to the content of the metal derived from the metal catalyst used in the polymerization reaction, i.e., 48 to 203 ppm.

(2) Washing of Copolymer

The metal catalyst content (in terms of a metal) is reduced to less than 1 ppm by washing the copolymer obtained above in step (1) in a mixed solvent containing acetic acid and isopropanol at a volume ratio of 25/75 to 45/55, at lower than 40° C.

First, it is preferable that the copolymer be pulverized using a grinder or the like into grains having an average particle diameter of about 0.3 to about 4 mm in order to improve the washing efficiency of the copolymer with a high metal content. The average particle diameter is measured using the following methods: Screening the particles using sieves having various mesh sizes, and calculating the average particle diameter based on the weight ratio of each of the screened portions; or taking a certain amount of the particles and observing the diameter of each of the particles by means of a microscope.

The washing solvent is a mixture comprising acetic acid and isopropanol. The mixed solvent has a function of permeating through the pulverized polymer to allow the acetic acid and metal catalyst to produce a chelate complex, which is to be extracted into the solution. The volume ratio of acetic acid and isopropanol in the mixed solvent is in the range of 25/75 to 45/55, and preferably in the range of 27/73 to 43/57. If necessary, a small amount of ethyl acetate can be added in addition to the isopropanol. In this case, the volume ratio of the isopropanol and the ethyl acetate is about 99/1 to about 70/30. The mixed solvent may be adjusted to have a pH of about 2 to about 6.

The content (bath ratio) of the mixed solvent used in the washing is, for example, not less than 1 L, preferably not less than 3 L, and more preferably in the range of about 3 to about 10 L per washing, relative to 1 kg of dry weight of the polymer. The washing method employed is such that the polymer is immersed in the mixed solvent having a temperature of less than 40° C., and preferably about 15 to about 30° C., and then stirred. The mixed solvent is changed 5 times or more, and preferably about 6 to about 12 times. The washing process takes a total of 48 hours or more, and preferably about 48 to about 96 hours.

In the early stages of washing, since a large amount of metal catalyst remains in the polymer, it is preferable that the bath ratio of the solvent be relatively increased (for example, about 4 to about 8 L relative to 1 kg of dry weight of the polymer), and/or that the exchange time of the washing solvent be shortened each time. During the latter half of the washing, it is preferable that the bath ratio of the solvent be minimized (about 3 to about 6 L relative to 1 kg of dry weight of the polymer), and/or that the washing time be prolonged.

Further, if necessary, it is preferable that the acetic acid be removed washing the polymer with isopropanol to prevent the molecular weight reduction after long storage.

The polymer after washing undergoes a drying process. The drying is conducted at about 15 to about 60° C., and preferably about 20 to about 50° C., for 6 hours or more, and preferably for about 10 to 150 hours, to remove an organic solvent. It is preferable that pre-drying be first preformed at about 20 to about 35° C. for about 10 to about 30 hours to remove isopropanol, and then drying be performed at about 35 to about 50° C. for about 40 to about 100 hours. Both drying processes are conducted under normal to reduced pressure (for example, about 0.01 to about 0.1 Pa), and are preferably conducted in vacuo at about 0.01 to about 0.05 Pa. The molecular weight reduction of the polymer can be prevented as much as possible by employing such drying conditions.

The biodegradable and bioabsorbable polymer of the present invention is produced in the aforementioned process. The metal catalyst content (in terms of a metal) of the biodegradable and bioabsorbable polymer is less than 1 ppm, preferably 0.1 to 0.95 ppm, more preferably 0.1 to 0.7 ppm, and further preferably 0.1 to 0.5 ppm.

The weight average molecular weight (Mw) of the biodegradable and bioabsorbable polymer is about 50,000 to about 800,000, preferably about 100,000 to about 650,000, and more preferably about 210,000 to about 500,000. Particularly, the retention rate of the weight average molecular weight of the copolymer after washing relative to that before washing is 75% or more, and further 80% or more. According to the method of the present invention, the molecular weight reduction during the washing process can be suppressed as much as possible.

3. Application

The biodegradable and bioabsorbable polymer of the present invention has an extremely low metal catalyst content of less than 1 ppm (in terms of a metal), and is safe when embedded in the body. Another feature of the invention is its easy general fabrication. Therefore, it is suitably used as a material for a medical device (a medical implant, etc.). Examples of medical implants include sutures, bone-joining materials, fracture fixation materials, tissue supplementation materials, tissue reinforcing materials, tissue covering materials, tissue regenerating base materials, tissue prosthetic materials, anti-adhesive materials, artificial blood vessels, artificial valves, stents, clips, fiber cloths, hemostatic materials, adhesives, coating agents, etc., which can be made by known production methods.

Second Embodiment

1. Biodegradable and Bioabsorbable Polymer

The biodegradable and bioabsorbable polymer of the present invention is a lactide/ε-caprolactone copolymer, which comprises lactide and ε-caprolactone at a molar ratio ranging from 65/35 to 85/15, and preferably 70/30 to 80/20.

The biodegradable and bioabsorbable polymer of the invention has a weight average molecular weight (Mw) of about 50,000 to about 800,000, and particularly about 100,000 to about 500,000. Within the range described above, the polymer is suitably used as a medical implant in view of properties such as strength, degradability, and processability.

A metal included in the biodegradable and bioabsorbable polymer is derived from a metal catalyst used in a polymerization reaction for producing the biodegradable and bioabsorbable polymer mentioned below. Examples of such metals include sodium, potassium, aluminium, titanium, zinc, tin, etc. For example, when tin octylate is used in the polymerization reaction, tin will be the main metal contained in the polymer.

The biodegradable and bioabsorbable polymer of the present invention has an extremely low metal catalyst content of less than 1 ppm in terms of a metal. The content of the metal catalyst (in terms of a metal) in the polymer is preferably 0.1 to 0.95 ppm, more preferably 0.1 to 0.7 ppm, and further preferably 0.1 to 0.5 ppm. Thus, even when the biodegradable and bioabsorbable polymer of the invention is used as a medical implant, there is little possibility of causing immunotoxicity, genetic toxicity, neurotoxicity, etc. in the human body.

The metal catalyst content (in terms of a metal) is measured as follows. A sulfuric acid/nitric acid mixture (1:1 volume ratio) is added to the polymer, and then heated to degrade an organic component. Metal in the resulting mixture is quantified using a plasma emission spectrometry machine with reference to a metal standard solution. Test Example II-1(1) illustrates a measurement example in which tin octylate is used as a catalyst.

2. Production of Biodegradable and Bioabsorbable Polymer

The biodegradable and bioabsorbable polymer of the present invention having a low metal catalyst content is produced by polymerizing lactide and ε-caprolactone in the presence of a metal catalyst to produce a copolymer, washing the copolymer with a mixed solvent comprising acetic acid and isopropanol at a volume ratio ranging from 45/55 to 55/45, and drying the copolymer. According to the production method, the metal catalyst content (in terms of a metal) in the biodegradable and bioabsorbable polymer can be reduced to less than 1 ppm.

The production method is explained in detail below.

(1) Production of Copolymer

The copolymer is produced by copolymerizing lactide and ε-caprolactone in the presence of a metal catalyst.

A lactic acid forming the lactide may be any one of the following: L-form, D-form, or DL-form, but is preferably L-form.

Examples of metal catalysts include those containing sodium, potassium, aluminium, titanium, zinc, tin, or like groups. Specific examples include sodium ethoxide, potassium-t-butoxide, triethylaluminum, tetrabutyl titanate, tin octylate (II), tin 2-ethylhexanoate, triphenyltin acetate, tin oxide, dibutyltin oxide, tin oxalate, tin chloride, dibutyltin dilaurate, etc. Of these, tin octylate (II) is preferable in view of reactivity and safety in the polymerization reaction.

The used amount of the metal catalyst is about 100 to about 1,000 ppm (about 29 to about 290 ppm in terms of a metal), and preferably about 200 to about 700 ppm (48 to 203 ppm in terms of a metal) relative to the mixture weight content of lactide and ε-caprolactone.

By using the metal catalyst in the range described above, a copolymer that has a molecular weight, strength, or like properties suitable for implant applications can be produced in a shorter period of time. When the amount of metal catalyst to be added is too small, a large number of monomers remain unreacted, or the reaction requires too much time, resulting in a polymer that is unsuitable for industrial manufacture. Further, a polymer having a large polymerization degree (a high molecular weight) cannot be obtained, and it is thus not preferable.

The copolymer can be produced by subjecting lactide and ε-caprolactone to a publicly known polymerization reaction such as bulk polymerization, in the presence of a metal catalyst. Specifically, the lactide and ε-caprolactone are introduced in a reaction vessel, and then the metal catalyst is added thereto such that the metal catalyst is contained in an amount of about 200 to about 700 ppm (48 to 203 ppm in terms of a metal). Bulk polymerization is then carried out under a nitrogen atmosphere, or under reduced pressure according to a known method for 2 to 20 days at 110 to 180° C.

The weight average molecular weight (Mw) of the resulting lactic acid-ε-caprolactone copolymer is about 50,000 to about 800,000, and preferably about 100,000 to about 500,000.

At this stage, the content of the metal catalyst (in terms of a metal) in the copolymer is equivalent to the content of the metal derived from the metal catalyst used in the polymerization reaction, i.e., 48 to 203 ppm.

(2) Washing of Copolymer

The metal catalyst content (in terms of a metal) is reduced to less than 1 ppm by washing the copolymer obtained above in step (1) in a mixed solvent containing acetic acid and isopropanol at a volume ratio of 45/55 to 55/45 at lower than 40° C.

First, it is preferable that the copolymer be pulverized using a grinder or the like into particles having an average particle diameter of about 0.3 to about 4 mm in order to improve the washing efficiency of the copolymer with a high metal content. The average particle diameter is measured using the following methods: Screening the particles using sieves having various mesh sizes, and calculating the average particle diameter based on the weight ratio of each of the screened portions; or taking a certain amount of the particles, and observing the diameter of each of the particles by means of a microscope. The washing solvent is a mixture comprising acetic acid and isopropanol. The mixed solvent has a function of permeating through the pulverized polymer to allow the acetic acid and metal catalyst to produce a chelate complex, which is to be extracted into the solution. The volume ratio of acetic acid and isopropanol in the mixed solvent is in the range of 45/55 to 55/45, and preferably in the range of 47/53 to 53/47. If necessary, a small amount of ethyl acetate can be added in addition to the isopropanol. In this case, the amount of ethyl acetate is 20% or less by volume, and preferably about 10% by volume relative to the amount of isopropanol.

The content (bath ratio) of the mixed solvent used in the washing is, for example, not less than 1 L, preferably not less than 3 L, and more preferably in the range of about 3 to about 10 L per washing, relative to 1 kg of dry weight of the polymer. The washing method employed is such that the polymer is immersed in the mixed solvent having a temperature of less than 40° C., and preferably about 15 to about 30° C., and then stirred. The mixed solvent is changed 4 times or more, and preferably about 5 to about 9 times. The washing process takes a total of 30 hours or more, and preferably about 30 to about 72 hours.

In the early stages of washing, since a large amount of metal catalyst remains in the polymer, it is preferable that the bath ratio of the solvent be relatively increased (for example, about 4 to about 8 L relative to 1 kg of dry weight of the polymer), and/or that the exchange time of the washing solvent be shortened each time. During the latter half of the washing, it is preferable that the bath ratio of the solvent be minimized (about 3 to about 6 L relative to 1 kg of dry weight of the polymer), and/or that the washing time be prolonged.

Further, if necessary, it is preferable that the acetic acid be removed by washing the polymer with isopropanol to prevent the molecular weight reduction after long storage.

The polymer after washing undergoes a drying process. The drying is conducted at about 15 to about 60° C., and preferably about 20 to about 50° C., for 6 hours or more, and preferably for about 10 to 150 hours, to remove an organic solvent. It is preferable that pre-drying be first performed at about 20 to about 35° C. for about 10 to about 30 hours to remove isopropanol, and then drying be performed at about 35 to about 50° C. for about 40 to about 100 hours. Both drying processes are conducted under normal to reduced pressure (for example, about 0.01 to about 0.1 Pa), and are preferably conducted in vacuo at about 0.01 to about 0.05 Pa. The molecular weight reduction of the polymer can be prevented as much as possible by employing such drying conditions.

The biodegradable and bioabsorbable polymer of the present invention is produced in the aforementioned process. The metal catalyst content (in terms of a metal) of the biodegradable and bioabsorbable polymer is less than 1 ppm, preferably 0.1 to 0.95 ppm, more preferably 0.1 to 0.7 ppm, and further preferably 0.1 to 0.5 ppm.

The weight average molecular weight (Mw) of the biodegradable and bioabsorbable polymer is about 50,000 to about 800,000, preferably about 100,000 to about 650,000, and more preferably about 210,000 to about 500,000. Particularly, the retention rate of the weight average molecular weight of the copolymer after washing relative to that before washing is 75% or more, and further 80% or more. According to the method of the present invention, the molecular weight reduction during the washing process can be suppressed as much as possible.

3. Application

The biodegradable and bioabsorbable polymer of the present invention has an extremely low metal catalyst content of less than 1 ppm (in terms of a metal), and is safe when embedded in the body. Another feature of the invention is its easy general fabrication. Therefore, it is suitably used as a material for a medical device (a medical implant, etc.). Examples of medical implants include sutures, bone-joining materials, fracture fixation materials, tissue supplementation materials, tissue reinforcing materials, tissue covering materials, tissue regenerating base materials, tissue prosthetic materials, anti-adhesive materials, artificial blood vessels, artificial valves, stents, clips, fiber cloths, hemostatic materials, adhesives, coating agents, etc., which can be made by known production methods.

Effects of the Invention

According to the present inventions (First and Second Embodiments), a biodegradable and bioabsorbable polymer having a reduced content of metal derived from a metal catalyst used in a polymerization reaction, and a small reduction in molecular weight can be obtained by washing the polymer obtained after a lactide and c-caprolactone copolymerization reaction with a mixed solvent containing acetic acid and isopropanol at a specified ratio, and drying the polymer. The resulting biodegradable and bioabsorbable polymer is comparable to known polymers in physicochemical properties, and can be processed by a general industrial method. Thus, it is suitably used as a material for a medical application (a medical implant).

BEST MODE FOR CARRYING OUT THE INVENTION

Figure 1:
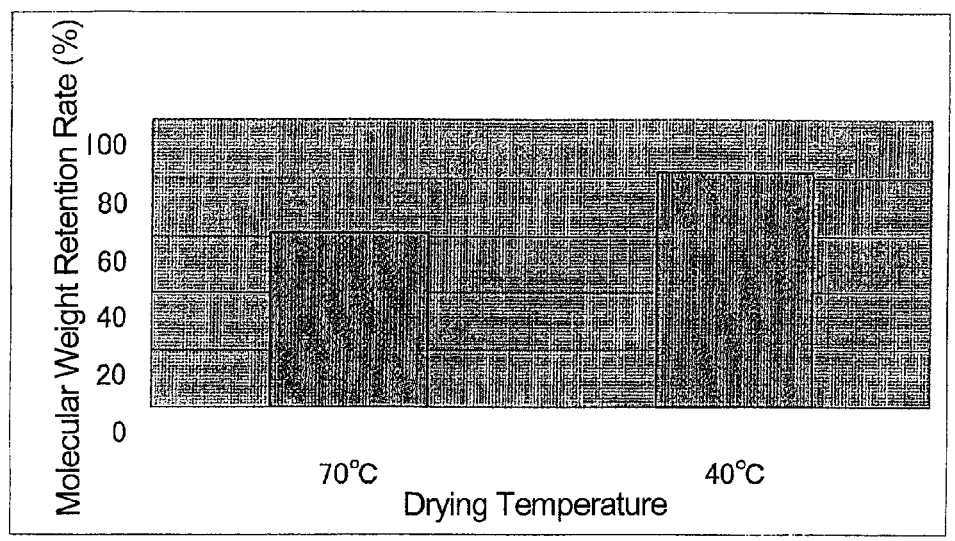
FIG. 1 is a graph showing the relationship between the drying temperature and the molecular weight retention rate of the polymer obtained in Test Example 1-3.

The invention will be described in detail below, with reference to Production Examples, Examples, and Test Examples.

First Embodiment

PRODUCTION EXAMPLE I-1

Lactide and ε-caprolactone (50:50, molar ratio) was introduced into a reaction glass tube, and 300 ppm of tin octylate (87 ppm in terms of a tin metal) was added thereto. Polymerization was performed under a nitrogen atmosphere using a known method to thereby obtain a polymer having a weight average molecular weight of 400,000. The polymer was pulverized using a grinder into a granulated polymer having a mean particle diameter of 3.0 mm. The amount of tin remaining in the polymer was 80 ppm.

The average particle diameter was determined from the weight ratio using sieves having different mesh sizes.

TEST EXAMPLE I-1

The polymer obtained in Production Example I-1 was immersed in, per 1 kg by weight of the polymer, 5 L of the mixed solution shown in Table 1, and stirred at 20° C. for 4 hours using a stirring device. The solution was replaced and stirred for 4 hours. Further, the solution was replaced, and stirred again for 16 hours. This series of procedures was repeated three times. Specifically, the polymer was washed with a solution having the same components nine times, for 72 hours in total. Subsequently, the polymer was immersed in 5 L of isopropanol, and stirred at 20° C. for one hour. Further, the solution was replaced, and washed under stirring with isopropanol for one hour.

The resulting polymer was vacuum-dried at 30° C. for 24 hours (0.01 Pa), and then vacuum-dried at 40° C. for 48 hours to remove a solvent.

The resulting polymer was measured for the metal catalyst content (residual tin content) and molecular weight retention rate. The results are shown in Table 1. The measuring methods are as follows.

(1) Measurement of Metal Catalyst Content

The resulting polymer was added to a sulfuric acid/nitric acid mixture (1:1, volume ratio), and gradually heated to degrade an organic component. A commercially available tin standard solution (tin chloride dihydrate, produced by Wako Pure Chemical Industries, Ltd.) was used as a standard, and quantified using a plasma emission spectrometry machine (a CID-AP model, produced by Nippon Jarrell-Ash Co. Ltd.).

(2) Measurement of Molecular Weight

The polymer was dissolved in chloroform, and the weight average molecular weight (Mw) was measured by gel permeation chromatography (GPC) using polystyrene standards. The molecular weight retention rate (%) was obtained by the following formula.

The molecular weight retention rate (%)=(the weight average molecular weight of the polymer after washing)/(the weight average molecular weight of the polymer before washing)×100

TABLE 1

| | Volume Ratio of Washing Solvent (%) | | | Status Of Polymer | Residual Tin Content | Weight Retention Rate |
|---|---|---|---|---|---|---|
| | Acetic Acid | Isopropanol | Ethyl Acetate | | | |
| Comparative Example I-1 | 10% | 90% | — | Swelling | C | A |
| Comparative Example I-2 | 20% | 80% | — | Swelling | B | A |
| Example I-1 | 30% | 70% | — | Swelling | A | A |
| Example I-2 | 40% | 60% | — | Swelling | A | A |
| Comparative Example I-3 | 50% | 50% | — | Dissolution | | |
| Example I-3 | 30% | 65% | 5% | Swelling | A | A |

Residual Tin Content
A: less than 1 ppm, B: 1 to less than 6 ppm, C: 6 ppm or more
Molecular Weight Retention Rate
A: 75 to 100%, B: 60 to less than 75%, C: less than 60%

Table 1 reveals that the polymers of Examples I-1 to I-3 had a reduced residual tin content, which was derived from the metal catalyst, of less than 1 ppm, kept a high molecular weight retention rate after washing, and had no appearance problem. Further, there was little change in physical properties before and after washing.

Contrarily, in Comparative Examples I-1 and I-2, the molecular weight retention rate was excellent, but the residual tin content became larger. The polymer in Comparative Example I-3 was dissolved because acetic acid was contained in a large amount.

TEST EXAMPLE I-2

Relationship Between the Washing Temperature and the Residual Tin Content and Molecular Weight Retention Rate The polymer obtained in Production Example I-1 was immersed in, per 1 kg by weight of the polymer, 5 L of the mixed solution of Example I-1 shown in Table 1. Each solution was stirred at 20° C., 30° C., and 40° C. for 4 hours using a stirring device. The solution was replaced and stirred for 4 hours. Further, the solution was replaced, and stirred again for 16 hours. This series of procedures was repeated three times. Specifically, the mixture was washed with a solution having the same components nine times for 72 hours in total.

Twenty grams of the polymer was sampled during the washing process, specifically, after completion of each of the $3^{rd}$, $5^{th}$, $6^{th}$, $8^{th}$, and $9^{th}$ washing steps. The polymer sampled was immersed in 100 mL of isopropanol, and stirred at 20° C. for one hour using a stirring device. The solution was replaced and stirred for one hour. Specifically, the solution was washed with isopropanol alone for two hours in total. The resulting polymer was vacuum-dried at 30° C. for 24 hours (0.01 Pa), and vacuum-dried again at 40° C. for 48 hours (0.01 Pa) to remove a solvent.

The metal catalyst content (the residual tin content) and the molecular weight retention rate of the resulting polymer were measured. The results are shown in Table 2. The measuring method used was the same as that described in Test Example I-1.

Table 2 shows temporal changes of the washing temperature and residual tin content. Table 3 shows temporal changes of the washing temperature and molecular weight retention rate.

TABLE 2

| | Residual Tin Content (ppm) | | |
|---|---|---|---|
| Time (h) | 20° C. | 30° C. | 40° C. |
| 0 | 79 | 79 | 79 |
| 24 | 2.8 | 1.6 | 1.7 |
| 32 | 1.1 | 0.5 | 0.5 |
| 48 | 0.5 | 0.5 | |
| 56 | | | |
| 72 | | | |

Diagonal Parts: less than the detection limits (0.5 ppm)

TABLE 3

| | Molecular Weight Retention Rate (%) | | |
|---|---|---|---|
| Time (h) | 20° C. | 30° C. | 40° C. |
| 0 | 100 | 100 | 100 |
| 24 | 92 | 89 | 71 |
| 32 | 87 | 86 | 67 |
| 48 | 83 | 81 | 57 |
| 56 | 81 | 82 | 51 |
| 72 | 82 | 75 | 49 |

Table 2 reveals that the residual tin content was reduced at any temperature to less than 1 ppm by the washing method of the present invention. The time required for reducing the residual tin content to less than 1 ppm was the shortest when washing was conducted at 40° C.; however, Table 3 reveals that the molecular weight was greatly reduced with time at 40° C.

On the other hand, Table 2 shows that there was no remarkable difference in the time required to achieve a residual tin content of less than 1 ppm between the washing temperature of 20° C. and 30° C. Table 3 shows that the molecular weight retention rate at 20° C. was likely higher than at 30° C.

TEST EXAMPLE I-3

Relationship Between the Drying Temperature and the Molecular Weight Retention Rate The polymer obtained in Production Example I-1 underwent steps before the drying step in accordance with the washing method of Example I-1 of Test Example I-1. The polymer obtained after washing was dried at 30° C. for 24 hours, and then vacuum-dried (0.01 Pa) at 40° C. for 48 hours or at 70° C. for 12 hours to remove a solvent.

FIG. 1 reveals that the molecular weight retention rate of the polymer obtained by drying at 40° C. (Example I-1) is 82.2%; however, the molecular weight retention rate of the polymer obtained by drying at 70° C. was greatly reduced to 61.0%.

Second Embodiment

PRODUCTION EXAMPLE II-1

Lactide and ε-caprolactone (75:25, molar ratio) was introduced into a reaction glass tube, and 300 ppm of tin octylate (87 ppm in terms of a tin metal) was added thereto. Polymerization was performed under a nitrogen atmosphere using a known method to thereby obtain a polymer having a weight average molecular weight of 700,000. The polymer was pulverized using a grinder into a granulated polymer having a mean particle diameter of 3.0 mm. The amount of tin remaining in the polymer was 80 ppm.

The average particle diameter was determined from the weight ratio using sieves having different mesh sizes.

TEST EXAMPLE II-1

The polymer obtained in Production Example II-1 was immersed in, per 1 kg by weight of the polymer, 5 L of the mixed solution shown in Table 4, and stirred at 20° C. for 4 hours using a stirring device. The solution was replaced and stirred for 4 hours. Further, the solution was replaced, and stirred again for 16 hours. This series of procedures was repeated two times. Specifically, the polymer was washed with a solution having the same components six times for 48 hours in total. Subsequently, the polymer was immersed in 5 L of isopropanol, and stirred at 20° C. for one hour. Further, the solution was replaced, and washed under stirring with isopropanol for one hour.

The resulting polymer was vacuum-dried at 30° C. for 24 hours (0.01 Pa), and then vacuum-dried at 40° C. for 48 hours to remove a solvent.

The resulting polymer was measured for the metal catalyst content (residual tin content) and molecular weight. The results are shown in Table 4. The measuring methods are as follows.

(1) Measurement of Metal Catalyst Content

The resulting polymer was added to a sulfuric acid/nitric acid mixture (1:1, volume ratio), and gradually heated to degrade an organic component. A commercially available tin standard solution (tin chloride dihydrate, produced by Wako Pure Chemical Industries, Ltd.) was used as a standard, and quantified using a plasma emission spectrometry machine (a CID-AP model, produced by Nippon Jarrell-Ash Co. Ltd.).

(2) Measurement of Molecular Weight

The polymer was dissolved in chloroform, and the weight average molecular weight (Mw) was measured by gel permeation chromatography (GPC) using a polystyrene standard as a standard. The molecular weight retention rate (%) was obtained by the following formula.

The molecular weight retention rate (%)=(the weight average molecular weight of the polymer after washing)/(the weight average molecular weight of the polymer before washing)×100

TABLE 4

| | Volume Ratio of Washing Solvent % | | | | | Status Of Polymer | Residual Tin Content | Molecular Weight Retention Rate |
|---|---|---|---|---|---|---|---|---|
| | Acetic Acid | Isopropanol | Ethyl Glycol | Acetone | Ethyl Acetate | | | |
| Comparative Example II-1 | 50% | | | 50% | — | Dissolution | | |
| Comparative Example II-2 | 50% | | 25% | | 25% | Swelling | B | C |
| Comparative Example II-3 | 10% | 80% | | | 10% | Swelling | B | A |
| Comparative Example II-4 | 10% | 90% | | | — | Swelling | C | A |
| Comparative Example II-5 | 30% | 70% | | | — | Swelling | B | A |
| Example II-1 | 50% | 50% | | | — | Swelling | A | A |
| Comparative Example II-6 | 70% | 30% | | | | Dissolution | | |

Residual Tin Content
A: less than 1 ppm, B: 1 to less than 6 ppm, C: 6 ppm or more
Molecular Weight Retention Rate
A: 75 to 100%, B: 60 to less than 75%, C: less than 60%

Table 4 reveals that the polymer of Examples II-1 had a reduced residual tin content, which was derived from the metal catalyst, of less than 1 ppm, kept a high molecular weight retention rate after washing, and had no appearance problem. Further, there was little change in physical properties before and after washing.

Contrarily, in Comparative Examples II-2 to II-5, the residual tin content exceeded 1 ppm, and further the molecular weigh retention rate was greatly reduced in Comparative Example II-2. The polymer in Comparative Examples II-1 and 11-6 was dissolved.

TEST EXAMPLE II-2

Relationship Between the Washing Temperature and the Residual Tin Content and Molecular Weight Retention Rate The polymer obtained in Production Example II-1 was immersed in, per 1 kg by weight of the polymer, 5 L of the mixed solution of Example II-1 shown in Table 4. Each solution was stirred at 20° C. or 40° C. for 4 hours using a stirring device. The solution was replaced and stirred for 4 hours. Further, the solution was again replaced, and stirred again for 16 hours. This series of procedures was repeated two times. Specifically, the mixture was washed with a solution having the same components six times for 48 hours in total.

Twenty grams of the polymer was sampled during the washing process, specifically, after completion of each of the $2^{nd}$, $3^{rd}$, $5^{th}$, and $6^{th}$ washing steps. The polymer sampled was immersed in 100 mL of isopropanol, and stirred at 20° C. for one hour using a stirring device. The solution was replaced and stirred for one hour. Specifically, the solution was washed with isopropanol alone for two hours in total. The resulting polymer was vacuum-dried at 30° C. for 24 hours (0.01 Pa), and vacuum-dried again at 40° C. for 48 hours (0.01 Pa) to remove a solvent.

Table 5 shows temporal changes of the washing temperature and residual tin content. Table 6 shows temporal changes of the washing temperature and molecular weight retention rate.

TABLE 5

Residual Tin Content (ppm)

| Time (h) | 20° C. | 40° C. |
|---|---|---|
| 0 | 73 | 73 |
| 8 | 3.6 | 1.6 |
| 24 | 1.0 | 0.4 |
| 32 | 0.5 | |
| 48 | 0.5 | |

TABLE 6

Molecular Weight Retention Rate (%)

| Time (h) | 20° C. | 40° C. |
|---|---|---|
| 0 | 100 | 100 |
| 8 | 92 | 79 |
| 24 | 90 | 71 |
| 32 | 91 | 53 |
| 48 | 95 | 46 |

Table 5 reveals that the residual tin content was reduced at any temperature to less than 1 ppm by the washing method of the present invention. The time required for reducing the residual tin content to less than 1 ppm was shorter when the washing was conducted at 40° C.; however, Table 6 reveals that the molecular weight was reduced with time at 40° C. On the other hand, the molecular weight retention rate was kept at a high rate (90% or more) at a washing temperature of 20° C.

TEST EXAMPLE II-3

Relationship Between the Drying Temperature and the Molecular Weight Retention Rate The polymer obtained in Production Example II-1 underwent steps before the drying step in accordance with the washing method of Example II-1 of Test Example II-1. The polymer obtained after washing was dried at 30° C. for 24 hours, and then vacuum-dried (0.01 Pa) at 40° C. for 48 hours or at 70° C. for 12 hours to remove a solvent.

Figure 2:
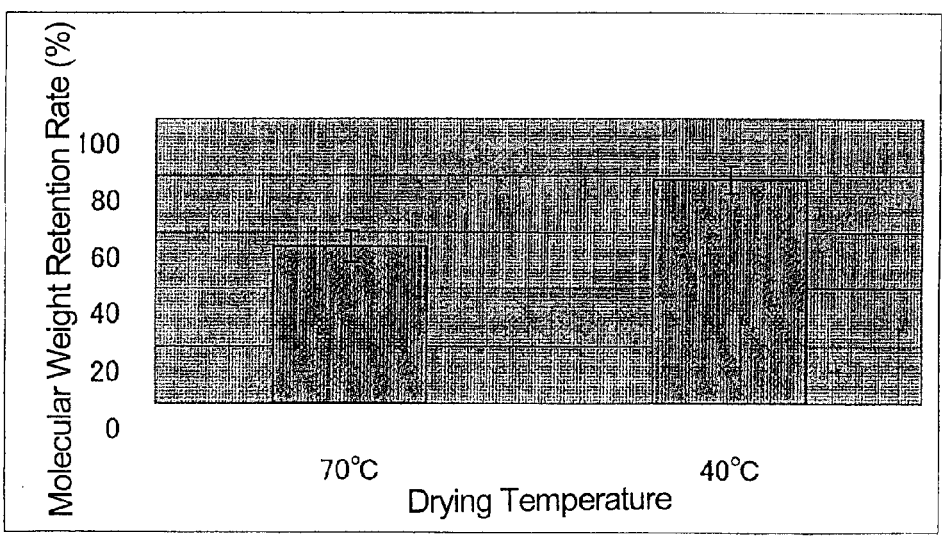
FIG. 2 is a graph showing the relationship between the drying temperature and the molecular weight retention rate of the polymer obtained in Test Example II-3.

FIG. 2 reveals that the molecular weight retention rate of the polymer obtained by drying at 40° C. (Example II-1) is 78.7%; however, the molecular weight retention rate of the polymer obtained by drying at 70° C. is greatly reduced to 54.6%.

What is claimed is:

1. A method for producing a biodegradable and bioabsorbable polymer having a metal catalyst content of less than 1 ppm in terms of a metal and having a weight average molecular weight of 100,000 to 800,000,
the method being selected from the group consisting of the following Methods (A) and (B):

Method (A) comprising the steps of,
(A1) polymerizing lactide and ε-caprolactone at a molar ratio ranging from 40/60 to 60/40 in the presence of a metal catalyst to produce a copolymer, and
(A2) washing the copolymer with a mixed solvent comprising acetic acid and isopropanol at a volume ratio ranging from 25/75 to 45/55 at less than 40° C., and drying the copolymer; or Method (B) comprising the steps of,
(B1) copolymerizing lactide and ε-caprolactone at a molar ratio ranging from 65/35 to 85/15 in the presence of the metal catalyst to produce a copolymer, and
(B2) washing the copolymer with a mixed solvent comprising acetic acid and isopropanol at a volume ratio ranging from 45/55 to 55/45 at less than 40° C., and drying the copolymer.

2. The method according to claim 1, wherein the method is Method (A).

3. The method according to claim 2, wherein a lactic acid forming the lactide in Step (A1) is L-form, D-form, or DL-form.

4. The method according to claim 2, wherein the temperature of the mixed solvent during the washing in Step (A2) is about 15° C. to about 30° C.

5. The method according to claim 2, wherein the mixed solvent is exchanged five times or more, and the washing time is a total of 48 hours or more in Step (A2).

6. The method according to claim 2, wherein the metal catalyst is at least one member selected from the group consisting of tin octylate (II), tin 2-ethylhexanoate, triphenyltin acetate, tin oxide, dibutyltin oxide, tin oxalate, tin chloride, and dibutyltin dilaurate.

7. The method according to claim 2, wherein the copolymer after washing is vacuum-dried at about 20° C. to about 35° C. for about 10 to about 30 hours, and then vacuum-dried at about 35° C. to about 50° C. for about 40 to about 100 hours.

8. The method according to claim 1, wherein the method is Method (B).

9. The method according to claim 8, wherein a lactic acid forming the lactide in Step (B1) is L-form, D-form, or DL-form.

10. The method according to claim 8, wherein the temperature of the mixed solvent during washing in Step (B2) is about 15° C. to about 30° C.

11. The method according to claim 8, wherein the mixed solvent is exchanged four times or more, and the washing time is a total of 30 hours or more in Step (B2).

12. The method according to claim 8, wherein the metal catalyst is at least one member selected from the group consisting of tin octylate (II), tin 2-ethylhexanoate, triphenyltin acetate, tin oxide, dibutyltin oxide, tin oxalate, tin chloride, and dibutyltin dilaurate.

13. The method according to claim 8, wherein the copolymer after washing is vacuum-dried at about 20° C. to about 35° C. for about 10 to about 30 hours, and then vacuum-dried at about 35° C. to about 50° C. for about 40 to about 100 hours.

14. A method of reducing the content of a metal catalyst in a biodegradable and bioabsorbable polymer to less than 1 ppm in terms of a metal, the polymer having a weight average molecular weight of 100,000 to 800,000,
the method being selected from the group consisting of the following Methods (A) and (B):

Method (A) comprising the steps of,
(A1) polymerizing lactide and ε-caprolactone at a molar ratio ranging from 40/60 to 60/40 in the presence of a metal catalyst to produce a copolymer, and
(A2) washing the copolymer with a mixed solvent comprising acetic acid and isopropanol at a volume ratio ranging from 25/75 to 45/55 at less than 40° C., and drying the copolymer; or Method (B) comprising the steps of,
(B1) copolymerizing lactide and ε-caprolactone at a molar ratio ranging from 65/35 to 85/15 in the presence of the metal catalyst to produce a copolymer, and
(B2) washing the copolymer with a mixed solvent comprising acetic acid and isopropanol at a volume ratio ranging from 45/55 to 55/45 at less than 40° C., and drying the copolymer.

15. A method for producing a medical implant comprising a biodegradable and bioabsorbable polymer having a metal catalyst content of less than 1 ppm in terms of a metal and having a weight average molecular weight of 100,000 to 800,000,
the method being selected from the group consisting of the following Methods (A) and (B):

Method (A) comprising the steps of,
(A1) copolymerizing lactide and ε-caprolactone at a molar ratio ranging from 40/60 to 60/40 in the presence of a metal catalyst to produce a copolymer,
(A2) washing the copolymer with a mixed solvent comprising acetic acid and isopropanol at a volume ratio ranging from 25/75 to 45/55 at less than 40° C., and drying the copolymer, so that the metal catalyst content becomes less than 1 ppm in terms of a metal, and
(A3) forming the copolymer obtained in Step (A2) into the medical implant; or Method (B) comprising the steps of,
(B1) copolymerizing lactide and ε-caprolactone at a molar ratio ranging from 65/35 to 85/15 in the presence of a metal catalyst to produce a copolymer,
(B2) washing the copolymer with a mixed solvent comprising acetic acid and isopropanol at a volume ratio ranging from 45/55 to 55/45 at less than 40° C., and drying the copolymer, so that the metal catalyst content becomes less than 1 ppm in terms of a metal, and
(B3) forming the copolymer obtained in Step (B2) into the medical implant.

16. The method according to claim 15, wherein the medical implant is selected from the group consisting of sutures, bone-joining materials, fracture fixation materials, tissue supplementation materials, tissue reinforcing materials, tissue covering materials, tissue regenerating base materials, tissue prosthetic materials, anti-adhesive materials, artificial blood vessels, artificial valves, stents, clips, fiber cloths, hemostatic materials, adhesives, and coating agents.

* * * * *